United States Patent [19]

Bragante et al.

[11] Patent Number: 5,414,167
[45] Date of Patent: May 9, 1995

[54] PROCESS FOR PURIFYING 1,1,1-TRIFLUORO-2,2-DICHLOROETHANE FROM ISOMER 1,1,2-TRIFLUORO-1,2-DICHLOROETHANE

[75] Inventors: Letanzio Bragante, Padova; Paolo Cuzzato, Treviso; Antonio Masiero, Padova, all of Italy

[73] Assignee: Ausimont S.p.A., Milan, Italy

[21] Appl. No.: 234,708

[22] Filed: Apr. 28, 1994

Related U.S. Application Data

[63] Continuation of Ser. No. 147,088, Nov. 3, 1993, abandoned, which is a continuation of Ser. No. 961,374, Oct. 15, 1992, abandoned.

[30] Foreign Application Priority Data

Oct. 18, 1991 [IT] Italy .................................. MI91A2757

[51] Int. Cl.⁶ .............................................. C07C 17/38
[52] U.S. Cl. ...................................... 570/177; 570/151; 570/163; 570/178
[58] Field of Search ................ 570/151, 163, 177, 178

[56] References Cited

U.S. PATENT DOCUMENTS

| | | | |
|---|---|---|---|
| 3,349,137 | 10/1967 | Cropp et al. | 570/177 |
| 4,748,284 | 5/1988 | Gozzo et al. | 570/151 |
| 4,766,260 | 8/1988 | Manzer et al. | 570/168 |
| 4,925,993 | 5/1990 | Zawalski | 570/151 |
| 5,030,372 | 7/1991 | Manoque et al. | 570/151 |

FOREIGN PATENT DOCUMENTS

| | | |
|---|---|---|
| 0282005A1 | 9/1988 | European Pat. Off. . |
| 0317981 | 5/1989 | European Pat. Off. ............ 570/151 |
| 0357328A1 | 3/1990 | European Pat. Off. . |
| 0450467A2 | 10/1991 | European Pat. Off. . |
| 1139517 | 1/1969 | United Kingdom . |
| 9202476 | 2/1992 | WIPO ................ 570/163 |

Primary Examiner—Alan Siegel
Attorney, Agent, or Firm—M. B. Stiefel; E. M. Barnhard

[57] ABSTRACT

The 1,1,2-trifluoro-1,2-dichloroethane content is reduced or removed from 1,1,1-trifluoro-2,2-dichloroethane by contacting a gaseous mixture comprising said compounds with chrome oxide ($Cr_2O_3$) either as such or supported, at temperatures from 180° to 400° C.

8 Claims, No Drawings

PROCESS FOR PURIFYING 1,1,1-TRIFLUORO-2,2-DICHLOROETHANE FROM ISOMER 1,1,2-TRIFLUORO-1,2-DICHLOROETHANE

This is a continuation of U.S. application Ser. No.08/147,088, filed Nov. 3, 1993, now abandoned, which is a continuation of U.S. application Ser. No. 07/961,374, filed Oct. 15, 1992, now abandoned, both of which are incorporated herein by reference.

The present invention relates to a process for reducing or removing impurities consisting of isomer 1,1,2-trifluoro-1,2-dichloroethane (hereinafter referred to as A123a) from 1,1,1-trifluoro-2,2-dichloroethane (hereinafter referred to as A123 ).

The need for having available industrial processes for preparing A123 as free as possible from A123a has been recognized.

Such need is particularly recognized, for example, by the manufacturers of polyurethane foams, for the production of which A123 is used as foaming agent. In such case, the A123a contained therein decomposes and forms HCl, which corrodes the metal circuits of the plants.

The industrially most interesting processes for the preparation of A123 are based on the hydrofluorination of tetrachloroethylene in the gas phase, in the presence of proper catalysts.

Such a process is described for example in U.S. Pat. No. 4,766,260.

Such a preparation process gives always rise to A123a in amounts ranging from 5 to 20%, depending on the reaction conditions. Said product is difficult to be distilled-off from A123.

In principle it is possible to carry out the reaction under such conditions as to minimize the formation of A123a, for example by using high temperatures (about 360° C.); however this is of little practical interest because under such conditions the process selectivity towards A123 is too low, while unacceptable amounts of by-products are obtained.

It is also possible to reduce the A123a content in the final reaction product by subjecting the A123 and A123a mixture to a treatment with anhydrous HF in the presence of the same catalyst as is used for its preparation, thereby obtaining the preferential fluorination of A123a to 1,1,1,2-tetrafluoro-2-chloroethane (A124).

However, the selectivity of such reaction is not high enough, wherefore also the fluorination of considerable amounts of A123 occurs.

The Applicant has now surprisingly found a process —constituting the object of the present invention— which permits the reduction or removal of A123a from its mixtures with A123 by means of a highly selective and highly efficient reaction, said process consisting in reacting a gaseous mixture comprising said compounds with chrome oxide, either as such or supported, at temperatures ranging from 180° to 400° C., but preferably from 220° to 320° C.

Under such conditions, a dismutation of A123a to products easily removable from A123 takes place, and in a few cases also a conversion of A123a into A123, with sparing or no decomposition of the latter.

By "chrome oxide", whenever used herein, is meant $Cr_2O_3$, generally in the form of pellets, suitable for being used in fixed beds, as well as the chrome oxyfluorides.

Said chrome oxides are utilizable as such or, preferably, supported on aluminium trifluoride, comprising the crystallographic forms $\beta$, $\gamma$ and $\Delta$, the form $\gamma$ and/or $\beta$ being preferably prevailing.

The crystalline chrome oxides are preferred, although it is possible, for the purposes of the invention, to utilize also them in the amorphous form.

The carried catalyst can be prepared by impregnating the alumina with a water solution of a chrome salt, preferably the chloride, then by treating said impregnated alumina with HF at high temperature, until obtaining the desired alumina fluorination degree, which preferably, but not necessarily, corresponds to an $AlF_3$ content of at least 90 moles per cent of the original alumina. Such a process is described in U.S. Pat. No. 4,766,260. According to a preferred method, such a catalyst is prepared by impregnating $AlF_3$, obtained by at least partial fluorination of $Al_2O_3$, according to known techniques, with a water solution of $CrCl_3$, then by treating the impregnated $AlF_3$ with nitrogen, optionally in the presence of oxygen in order to promote the formation of the chrome oxide crystalline structure, and then with anhydrous HF in hot conditions.

Such a process is described for example in European patent application Ser. No. 282,005.

The use of a carrier makes the catalyst not only more efficient, but also suited to be used in fluidized bed reactors.

The chrome content of the carried catalysts ranges from 1 to 10% by weight, calculated as metallic chrome on the catalyst total weight.

The catalyst in the form of chrome oxide pellets can be prepared according to conventional methods, for example by precipitation of $Cr(OH)_3$ from solutions of a proper chrome salt, by subsequent extrusion and drying. Calcination at a temperature from 500° to 700° C. can follow in order to obtain $Cr_2O_3$ in the crystalline form.

The chrome oxide in pellets can be activated prior to reaction by heating to 300°–400° C. with anhydrous HF, preferably in the same reactor, in which it will be used as a catalyst.

In the reaction, the contact time of the gaseous mixture comprising A123 and A123a with the catalyst can vary over a wide range. Generally, said contact time ranges from 1 to 200 seconds, but preferably from 10 to 110 seconds. The pressure is not particularly critical; generally it is operated at atmospheric pressure or at a slightly higher pressure.

The catalyst activity is only very slightly affected by deactivation phenomena; in any case it can be restored by treatment with hot air.

The following examples are given to illustrate the invention but not to limit the scope thereof.

EXAMPLE 1

(A) An aluminium fluoride having a specific surface of about 26 m/g prepared by fluorination of $Al_2O_3$ with anhydrous HF up to an $AlF_3$ content of 94% by weight, was impregnated with a water solution of $CrCl_3.6H_2O$ in an amount of 492 g of $CrCl_3.6H_2O$ per kg of $AlF_3$, by means of one of the methods of the art, and was dried at 120°–150° C., so obtaining a catalyst containing 8% by weight of chrome. The utilized aluminium fluoride had a particle size ranging from 20 to 200 microns, on the average of 80 microns, and was composed for 20% of the $\Delta$ form and for 80% of the $\gamma$ form. 400 g of this catalyst were introduced into a tubular reactor made of Inconel 600 ®, having an inside diameter of 5 cm and a length of 80 cm, and equipped with a porous bottom of sintered Inconel 600.

(B) The catalyst introduced into the above-described reactor was heated up to 400° C. in a nitrogen flow for 10 hours, then it was treated with 80 g/h of anhydrous HF for 2-3 hours at 350° C. Lastly, the temperature was reduced to 240° C. and the feeding of 153 g/h (1 mole/h) of a mixture containing 80 moles-% of A123 and 20 moles-% of A123a was started. The gases leaving the reactor were bubbled in water in order to absorb acidity traces, were condensed and then analyzed by means of gas chromatography (G.C.). By varying the temperature and the contact time, the results reported in Table 1 were obtained.

TABLE 1

| Operative conditions and obtained products | | | |
|---|---|---|---|
| Composition obtained after reaction | Contact time = 25 seconds Temperature (°C.) | | Contact time = 50 seconds Temperature (°C.) |
| | 240 | 260 | 240 |
| A115 (moles-%) | 0.0 | 0.2 | 0.2 |
| A125 (moles-%) | 0.8 | 4.0 | 0.3 |
| A114 (moles-%) | 0.3 | 1.0 | 0.2 |
| A124 (moles-%) | 11.7 | 16.5 | 7.9 |
| A1112 (moles-%) | 0.1 | 0.1 | 0.0 |
| A133 (moles-%) | 0.2 | 0.8 | 0.1 |
| A113 (moles-%) | 0.1 | 0.2 | 0.2 |
| A123a (moles-%) | 4.2 | 1.6 | 6.7 |
| A123 (moles-%) | 74.4 | 65.7 | 77.3 |
| A1111* (moles-%) | 3.2 | 2.8 | 3.1 |
| A122* (moles-%) | 0.8 | 0.3 | 0.5 |
| A1120* (moles-%) | 0.2 | 0.7 | 0.0 |
| A1110* (moles-%) | 3.9 | 6.0 | 3.3 |

*Recyclable products
A115 = $CF_3CClF_2$
A143 = $CF_3CH_3$
A125 = $CF_3CHF_2$
A134a = $CF_3CH_2F$
A114 = $CClF_2CClF_2$
A124 = $CF_3CHClF$
A1112 = $CClF=CClF$
A133 = $CHF_2CHClF$
A113 = $CCl_2FCClF_2$
A1111 = $CClF=CCl_2$
A122 = $CHCl_2CClF_2$
A1120 = $CHClCCl_2$
A1110 = $CCl_2=CCl_2$

EXAMPLE 2

400 g of the catalyst prepared according to example 1 (A) were introduced into the reactor illustrated in said example and were fluidized for 10 hours at 400° C. in an air flow.

Utilizing a mixture of A123 and A123a in a molar ratio of 80/20, the results reported in Table 2 were obtained.

TABLE 2

| Operative conditions and obtained products | | | | |
|---|---|---|---|---|
| Composition obtained after reaction | T = 250° C. t = 18" | T = 250° C. t = 21,5" | T = 240° C. t = 23" | T = 220° C. t = 50" |
| A115 (moles-%) | 0.0 | 0.0 | 0.0 | 0.0 |
| A125 (moles-%) | 0.7 | 1.6 | 1.2 | 0.3 |
| A114 (moles-%) | 0.2 | 0.3 | 0.2 | 0.1 |
| A124 (moles-%) | 10.6 | 12.6 | 12.2 | 8.8 |
| A1112 (moles-%) | 0.1 | 0.1 | 0.1 | 0.1 |
| A133 (moles-%) | 0.1 | 0.2 | 0.2 | 0.1 |
| A113 (moles-%) | 0.2 | 0.1 | 0.1 | 0.1 |
| A123a (moles-%) | 1.7 | 0.3 | 0.4 | 2.3 |
| A123 (moles-%) | 80.4 | 76.3 | 79.2 | 83.4 |
| A1111* (moles-%) | 2.6 | 2.1 | 1.9 | 2.1 |
| A122* (moles-%) | 0.4 | 0.2 | 0.2 | 0.5 |
| A1120 (moles-%) | 0.1 | 0.2 | 0.1 | 0.0 |
| A1110* (moles-%) | 2.8 | 5.9 | 4.3 | 2.2 |

*Recyclable products

EXAMPLE 3

A water solution of $CrCl_3$ was treated with sodium hydroxide, thereby obtaining the precipitation of chrome hydroxide in the form of gel.

This gel was washed with water, dried in air at room temperature and the resulting paste was extruded in the form of little cylinders having a diameter of about 5 mm. These were calcined in air at 550° C., so obtaining $Cr_2O_3$ in the crystalline form, which was charged into the reactor of example 1.

Table 3 shows the results obtained by causing a A123/A123a mixture in a 80/20 molar ratio to flow over such catalyst.

TABLE 3

| Operative conditions and obtained products | | | | | | | | | |
|---|---|---|---|---|---|---|---|---|---|
| Composition obtained after reaction | T = 260° t = 24" | T = 300° t = 23" | T = 320° t = 22" | T = 260° t = 90" | T = 240° t = 82" | T = 220 t = 90" | T = 320° t = 45" | T = 300° t = 46" | T = 280° t = 47" |
| A115 (moles-%) | 0.1 | 0.1 | 0.1 | 0.1 | 0.0 | 0.0 | 0.1 | 0.0 | 0.0 |
| A125 (moles-%) | 0.0 | 1.2 | 3.4 | 2.1 | 1.4 | 0.4 | 2.9 | 1.1 | 5.0 |

TABLE 3-continued

| Operative conditions and obtained products | | | | | | | | | |
|---|---|---|---|---|---|---|---|---|---|
| Composition obtained after reaction | T = 260° t = 24" | T = 300° t = 23" | T = 320° t = 22" | T = 260° t = 90" | T = 240° t = 82" | T = 220 t = 90" | T = 320° t = 45" | T = 300° t = 46" | T = 280° t = 47" |
| A114 (moles-%) | 0.4 | 1.1 | 1.9 | 2.0 | 1.0 | 0.4 | 1.6 | 1.0 | 4.0 |
| A124 (moles-%) | 3.1 | 14.6 | 18.6 | 15.5 | 16.4 | 11.5 | 17.0 | 16.5 | 12.0 |
| A1112 (moles-%) | 0.1 | 0.2 | 0.3 | 0.1 | 0.1 | 0.1 | 0.2 | 0.2 | 2.0 |
| A133 (moles-%) | 0.1 | 0.3 | 0.5 | 0.5 | 0.6 | 0.4 | 0.4 | 0.5 | 0.4 |
| A113 (moles-%) | 0.8 | 0.6 | 0.6 | 0.8 | 0.5 | 0.5 | 0.7 | 0.6 | 0.5 |
| A123a (moles-%) | 12.0 | 3.7 | 1.4 | 0.5 | 1.8 | 4.7 | 1.0 | 2.1 | 5.4 |
| A123 (moles-%) | 80.6 | 68.8 | 58.5 | 65.1 | 67.9 | 72.2 | 59.6 | 66.2 | 72.0 |
| A1111* (moles-%) | 0.9 | 2.8 | 3.2 | 1.9 | 3.2 | 3.9 | 3.4 | 3.2 | 3.2 |
| A122* (moles-%) | 0.4 | 0.5 | 0.3 | 0.2 | 0.5 | 1.4 | 0.3 | 0.5 | 1.1 |
| A1120 (moles-%) | 0.1 | 0.9 | 2.2 | 1.1 | 0.7 | 0.3 | 2.3 | 1.3 | 0.6 |
| A1110* (moles-%) | 1.0 | 4.8 | 8.4 | 9.8 | 5.6 | 3.7 | 10.2 | 6.4 | 3.4 |

*Recyclable products

EXAMPLE 4

2.0 g of the catalyst of example 1 were charged into a tubular Inconel reactor having a diameter of 8 mm, The reactor was fed with 1.5 g/h of an organic mixture containing A123 (85.9%) and A123a (13.8%) and with 1.0 g/h of HF. The analysis of the outflowing gases was carried out via GLC at different reaction temperatures and with contact times of about 5-7 seconds. The following results were obtained:

| Temperature °C. | A123 % | A123a % | $CF_3CHFCl$ % | $CF_3CHF_2$ % |
|---|---|---|---|---|
| 240 | 88.3 | 11.5 | 0.14 | 0 |
| 280 | 86.0 | 9.5 | 4.5 | 0.04 |
| 320 | 60.6 | 2 | 34.3 | 3.08 |
| 360 | 31.7 | 0.2 | 42.9 | 25.5 |
| 380 | 20.1 | 0.2 | 23.7 | 56.2 |
| 400 | 17.2 | 0.3 | 20.8 | 62 |

EXAMPLE 5

2.35 g of a catalyst composed of $Al_2O_3$ pellets (4-8 meshes) impregnated with $CrCl_3.6H_2O$ were treated firstly with nitrogen, then with HF at 360° C. until obtaining an $AlF_3$ content equal to 59.5% by weight, then they were charged into a tubular Inconel reactor. The catalyst contained 5.8% by weight of chrome. A mixture composed of A123 (82.20%) and of A123a (17.47 was fed to the reactor at a temperature of 260° C., using different contact times; the outflowing gases were analyzed via GLC and the following results were obtained:

| Test No. | Contact time sec. | A123 moles-% | A123a moles-% | $CF_3CHFCl$ moles-% | $CF_3CHF_2$ moles-% |
|---|---|---|---|---|---|
| 1 | 2.5 | 77.5 | 2.2 | 15.7 | 0.68 |
| 2 | 11 | 79.6 | 0.27 | 15.1 | 0.33 |

There were treated about 3.1 g of gaseous mixture in test 1 and 1.0 g in test 2, whereafter the catalyst can be regenerated and reutilized several times.

We claim:

1. A process for selectively reducing or removing 1,1,2-trifluoro- 1,2-dichloroethane from its mixtures with 1,1,1-trifluoro-2,2-dichloroethane which comprises contacting a gaseous mixture comprising 1,1,2-trifluoro- 1,2-dichloroethane and 1,1,1-trifluoro-2,2-dichloroethane with a chrome oxide at temperatures ranging from 220° to 320° C. for a time ranging from 10 to 110 seconds under such conditions that dismutation of 1,1,2-trifluoro-1,2-dichloroethane occurs to yield a dismutation product, or products, removable from 1,1,1-tri-fluoro-2,2-dichloroethane.

2. A process for selectively reducing or removing 1,1,2-trifluoro- 1,2-dichloroethane from its mixtures with 1,1,1-trifluoro-2,2-dichloroethane which comprises contacting a gaseous mixture comprising 1,1,2-trifluoro- 1,2-dichloroethane and 1,1,1-trifluoro-2,2-dichloroethane with a chrome oxide carried on an aluminum trifluoride, at temperatures ranging from 220° to 320° C. for a time ranging from 10 to 110 seconds under such conditions that dismutation of 1,1,2-tri-fluoro-1,2-dichloroethane occurs to yield a dismutation product, or products, removable from 1,1,1-trifluoro-2,2-dichloroethane.

3. The process of claim 1 wherein the chrome oxide is in the crystalline form.

4. The process of claim 1, wherein the mixture of 1,1,2-trifluoro-1,2-dichloroethane and 1,1,1-trifluoro-2,2-dichloroethane is obtained in the preparation of 1,1,1-trifluoro-2,2-dichloroethane by hydrofluorination of perchloroethylene.

5. The process of claim 2, wherein the chrome oxide is in the crystalline form.

6. The process of claim 2, wherein the mixture of 1,1,2-trifluoro- 1,2-dichloroethane and 1,1,1-trifluoro-2,2-dichloroethane is obtained in the preparation of 1,1,1-trifluoro-2,2-dichloroethane by hydrofluorination of perchloroethylene.

7. The process of claim 1, further including the step of removing a dismutation product of 1,1,2-trifluoro- 1,2-dichloroethane from a mixture comprising 1,1,1-trifluoro-2,2-dichloroethane.

8. The process of claim 2, further including the step of removing a dismutation product of 1,1,2-trifluoro- 1,2-dichloroethane from the mixture comprising 1,1,1-trifluoro-2,2-dichloroethane.

* * * * *